United States Patent
Degering et al.

(10) Patent No.: US 10,494,622 B2
(45) Date of Patent: Dec. 3, 2019

(54) EXPRESSION VECTORS WITH PROMOTER AND NUCLEIC ACID

(71) Applicant: BASF SE, Ludwigshafen (DE)

(72) Inventors: Christian Degering, Erkrath (DE); Thorsten Eggert, Hattingen (DE); Stefan Evers, Mettmann (DE); Karl-Heinz Maurer, Erkrath (DE); Johannes Bongaerts, Dormagen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/712,652

(22) Filed: Sep. 22, 2017

(65) Prior Publication Data

US 2018/0073005 A1    Mar. 15, 2018

Related U.S. Application Data

(62) Division of application No. 14/122,562, filed as application No. PCT/EP2012/059901 on May 25, 2012, now Pat. No. 9,803,183.

(30) Foreign Application Priority Data

May 31, 2011    (DE) .......................... 10 2011 118 032

(51) Int. Cl.
   *C12N 9/50* (2006.01)
   *C12N 15/62* (2006.01)
   *C12N 15/70* (2006.01)
   *C12N 15/75* (2006.01)

(52) U.S. Cl.
   CPC ............. *C12N 9/50* (2013.01); *C12N 15/625* (2013.01); *C12N 15/70* (2013.01); *C12N 15/75* (2013.01)

(58) Field of Classification Search
   None
   See application file for complete search history.

(56) References Cited

U.S. PATENT DOCUMENTS

| | | | | |
|---|---|---|---|---|
| 7,494,798 B2 * | 2/2009 | Berka | ..................... | C07K 14/32 435/209 |
| 7,863,032 B2 * | 1/2011 | Berka | ..................... | C12Q 1/689 435/209 |
| 8,168,417 B2 * | 5/2012 | Berka | ..................... | C12Q 1/689 435/193 |
| 8,785,172 B2 | 7/2014 | Minning et al. | | |
| 2005/0003504 A1 | 1/2005 | Weber et al. | | |
| 2009/0275104 A1 | 11/2009 | Berka et al. | | |
| 2010/0196991 A1 | 8/2010 | O'Connell et al. | | |
| 2012/0135498 A1 | 5/2012 | Greiner-Stoeffele et al. | | |

FOREIGN PATENT DOCUMENTS

| | | |
|---|---|---|
| CA | 2831473 A1 | 10/2012 |
| DE | 102007049830 A1 | 4/2009 |
| WO | WO-91/02792 A1 | 3/1991 |
| WO | WO-92/21760 A1 | 12/1992 |
| WO | WO-2003/054185 A1 | 7/2003 |
| WO | WO-2004/111224 A1 | 12/2004 |
| WO | WO-2007/122175 A1 | 11/2007 |
| WO | WO-2008/066931 A2 | 6/2008 |
| WO | WO-2011/015327 A1 | 2/2011 |
| WO | WO-2012/139964 A1 | 10/2012 |
| WO | WO-2013/113689 A1 | 8/2013 |

OTHER PUBLICATIONS

Brockmeier et al., Systematic screening of all signal peptides from Bacillus subtilis: a powerful strategy in optimizing heterologous protein secretion in Gram-positive bacteria, J. Mol. Biol., 362(3):393-402 (2006).

Degering et al., Optimization of protease secretion in Bacillus subtilis and Bacillus licheniformis by screening of homologous and heterologous signal peptides, Appl. Environ. Microbiol., 76(19):6370-6 (2010).

Degering, Optimierung heterologer proteinsekretion in *Bacillus* unter verwendung wirtsfremder und Künstlicher signalpeptide, Inagural Dissertation, Universität Düsseldorf, pp. 1-143 (2010).

International Preliminary Report on Patentability, issued in PCT/EP2012/059901, dated Dec. 2, 2013.

International Search Report, issued in PCT/EP2012/059901, dated Sep. 19, 2012.

UniProtKB—P29599 (SUBB-BACLE), Protein Subtilisin BL (last sequence update: Apr. 1, 1993; last modified: Oct. 25, 2017).

Hirose et al., Proteome analysis of Bacillus subtilis extracellular proteins: a two-dimensional protein electrophoretic study, Microbiology, 146(Pt.1):65-75 (2000).

European Patent Application No. 18212311.7, European Search Report, dated May 17, 2019.

* cited by examiner

*Primary Examiner* — Hope A Robinson
(74) *Attorney, Agent, or Firm* — Marshall, Gerstein & Borun LLP

(57) ABSTRACT

The aim of the invention is to improve the secretion of a protein from a host cell in order to increase the product yield of protein in a fermentation process. This is achieved by an expression vector comprising a) a promoter sequence and b) a nucleic acid sequence that codes for a protein. The protein comprises a signal peptide and an additional amino acid sequence, and the signal peptide comprises an amino acid sequence that is at least 80% identical to the amino acid sequence specified in SEQ ID NO: 2, at least 80% identical to the amino acid sequence specified in SEQ ID NO: 4, at least 80% identical to the amino acid sequence specified in SEQ ID NO: 6, or the signal peptide comprises an amino acid sequence that is structurally homologous to at least one of said sequences.

11 Claims, 3 Drawing Sheets
Specification includes a Sequence Listing.

EXPRESSION VECTORS WITH PROMOTER AND NUCLEIC ACID

This application is a divisional of U.S. patent application Ser. No. 14/122,562, now U.S. Pat. No. 9,803,183, which is the U.S. National Stage application of International Application No. PCT/EP2012/059901, filed May 25, 2012, and also claims priority under 35 U.S.C. § 119 to German Patent Application No. 10 2011 118 032.3, filed May 31, 2011; all of these applications are incorporated by reference herein in their entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "75519A_Seqlisting.txt", which was created on Sep. 19, 2017 and is 14,920 bytes in size. The subject matter of the Sequence Listing is incorporated herein in its entirety by reference.

The invention is in the field of biotechnology, more particularly microbial protein synthesis. The invention relates in particular to expression vectors for preparing proteins and proposes, in addition, host cells comprising such expression vectors. The invention further relates to methods and uses of such expression vectors and host cells for protein preparation.

For the preparation of proteins, use can be made of host cells, more particularly microorganisms, expressing the genes of the proteins of interest. The gene of a protein of interest (transgene) is generally introduced into the host cells in such a way that it is expressed thereby. Frequently, it is present on a so-called expression vector together with one or more promoter sequences (promoters), which permit gene expression.

For industrial-scale, biotechnological production, the host cells in question are cultured in fermenters which are adapted accordingly to the metabolic properties of the cells. During the culture, the host cells metabolize the supplied substrate and form the desired product, which, after the end of the fermentation, is usually separated from the production organisms and is purified and/or concentrated from the fermenter slurry and/or the fermentation medium.

It is inherently desirable to obtain a very high product yield in the fermentation. The product yield is dependent on multiple factors, for example the host cells usually form, in addition to the product actually desired, a multiplicity of further substances which are generally of no interest. In addition, the expression of a transgene and thus the product yield depends substantially on the expression system used. For example, the international patent application WO 91/02792 discloses the improved fermentative production of an alkaline protease from *Bacillus lentus* in an optimized *Bacillus licheniformis* strain under the control of gene regulatory sequences from *Bacillus licheniformis*, more particularly the *Bacillus licheniformis* promoter.

For the industrial production of proteins, for example hydrolytic enzymes, preference is given to using host cells capable of secreting large amounts of the protein into the culture supernatant, making elaborate cell disruption, which is necessary in intracellular production, redundant. For this purpose, preference is given to using host cells, for example *Bacillus* species, which can be cultured using cost-effective culture media in efficient high-cell-density fermentation procedures and are capable of secreting multiple grams per liter of the target protein into the culture supernatant. Usually, the protein to be secreted is expressed by expression vectors which have been introduced into the host cell and encode the protein to be secreted. The expressed protein usually comprises a signal peptide (signal sequence) which brings about the export thereof from the host cell. The signal peptide is usually part of the polypeptide chain translated in the host cell, but it can be additionally cleaved posttranslationally from the protein inside or outside the host cell.

Especially for this extracellular production of heterologous proteins, there are, however, numerous bottlenecks and a corresponding high demand for optimization of the secretion processes. One of these bottlenecks is the selection of a signal peptide which allows efficient export of the target protein from the host cell. Signal peptides can, in principle, be newly combined with proteins, more particularly enzymes. For example, the publication by Brockmeier et al. (J. Mol. Biol. 362, pages 393-402 (2006)) describes the strategy of screening a signal peptide library using the example of a cutinase. However, not every signal peptide also brings about adequate export of the protein under fermentation conditions, more particularly industrial or industrial-scale fermentation conditions.

It is therefore an object of the invention to improve the secretion of a protein from a host cell and, as a result, to increase the protein product yield in a fermentation procedure.

The invention provides an expression vector comprising
a) a promoter sequence and
b) a nucleic acid sequence which encodes a protein, the protein comprising a signal peptide and a further amino acid sequence and the signal peptide comprising an amino acid sequence which is at least 80% identical to the amino acid sequence specified in SEQ ID NO: 2 or is at least 80% identical to the amino acid sequence specified in SEQ ID NO: 4 or is at least 80% identical to the amino acid sequence specified in SEQ ID NO: 6, or the signal peptide comprising an amino acid sequence which is structurally homologous to at least one of these sequences.

It was found that, surprisingly, an expression vector encoding a protein having such a signal peptide achieves improved secretion of the protein from a host cell containing the expression vector and expressing the nucleic acid sequence b). As a result, it is possible in preferred embodiments of the invention to increase the protein product yield in a fermentation procedure.

An expression vector is a nucleic acid sequence which enables the protein to be expressed in a host cell, more particularly a microorganism. It comprises the genetic information, i.e., that nucleic acid sequence (gene) b) which encodes the protein.

The expression of a nucleic acid sequence is its rendering into the gene product(s) encoded by said sequence, i.e., into a polypeptide (protein) or into multiple polypeptides (proteins). The terms polypeptide and protein are used synonymously in the present application. For the purposes of the present invention, expression consequently means the biosynthesis of ribonucleic acid (RNA) and proteins from the genetic information. Generally, the expression comprises the transcription, i.e., the synthesis of a messenger ribonucleic acid (mRNA) on the basis of the DNA (deoxyribonucleic acid) sequence of the gene, and the translation of the mRNA into the corresponding polypeptide chain, which may additionally be modified posttranslationally. The expression of a protein consequently describes the biosynthesis thereof from the genetic information which is provided according to the invention on the expression vector.

Vectors are genetic elements consisting of nucleic acids, preferably deoxyribonucleic acid (DNA), and are known to a person skilled in the art in the field of biotechnology. Particularly when used in bacteria, they are specific plasmids, i.e., circular genetic elements. The vectors can, for example, include those which are derived from bacterial plasmids, from viruses or from bacteriophages, or predominantly synthetic vectors or plasmids containing elements of very diverse origin. With the further genetic elements present in each case, vectors are capable of establishing themselves in host cells, into which they have been introduced preferably by transformation, over multiple generations as stable units. In this respect, it is insignificant for the purposes of the invention whether they are established extrachromosomally as separate units or are integrated into a chromosome or chromosomal DNA. Which of the numerous systems is chosen depends on the individual case. Critical factors may, for example, be the achievable copy number, the selection systems available, including especially the antibiotic resistances, or the culturability of the host cells capable of vector uptake.

Expression vectors may, furthermore, be regulatable through changes in the culture conditions, for example the cell density or the addition of particular compounds. An example of such a compound is the galactose derivative isopropyl-β-D-thiogalactopyranoside (IPTG), which is used as an activator of the bacterial lactose operon (lac operon).

An expression vector further comprises at least one nucleic acid sequence, preferably DNA, having a control function for the expression of the nucleic acid sequence b) encoding the protein (a so-called gene regulatory sequence). A gene regulatory sequence is, in this case, any nucleic acid sequence which, through its presence in the particular host cell, affects, preferably increases, the transcription rate of the nucleic acid sequence b) which encodes the protein. Preferably, it is a promoter sequence, since such a sequence is essential for the expression of the nucleic acid sequence b). However, an expression vector according to the invention can also comprise yet further gene regulatory sequences, for example one or more enhancer sequences. An expression vector for the purposes of the invention consequently comprises at least one functional unit composed of the nucleic acid sequence b) and a promoter (expression cassette). It can, but need not necessarily, be present as a physical entity. The promoter brings about the expression of the nucleic acid sequence b) in the host cell. For the purposes of the present invention, an expression vector can also be restricted to the pure expression cassette composed of promoter and nucleic acid sequence b) to be expressed, it being possible for said expression cassette to be integrated extrachromosomally or else chromosomally. Such embodiments of expression vectors according to the invention each constitute a separate embodiment of the invention.

The presence of at least one promoter is consequently essential for an expression vector according to the invention. A promoter is therefore understood to mean a DNA sequence which allows the regulated expression of a gene. A promoter sequence is naturally a component of a gene and is often situated at the 5' end thereof and thus before the RNA-coding region. Preferably, the promoter sequence in an expression vector according to the invention is situated 5' upstream of the nucleic acid sequence b) encoding the protein. The most important property of a promoter is the specific interaction with at least one DNA-binding protein or polypeptide which mediates the start of the transcription of the gene by means of an RNA polymerase and is referred to as a transcription factor. Multiple transcription factors and/or further proteins are frequently involved at the start of the transcription by means of an RNA polymerase. A promoter is therefore preferably a DNA sequence having promoter activity, i.e., a DNA sequence to which at least one transcription factor binds at least transiently in order to initiate the transcription of a gene. The strength of a promoter is measurable via the transcription rate of the expressed gene, i.e., via the number of RNA molecules, more particularly mRNA molecules, generated per unit time.

Preferably, the promoter sequence (a) and the nucleic acid sequence (b) are behind one another on the expression vector. More preferably, the promoter sequence (a) is situated ahead of the nucleic acid sequence (b) on the nucleic acid molecule (in the 5'→3' orientation). It is likewise preferred that, between the two nucleic acid sequences (a) and (b), there are no nucleic acid sequences which reduce the transcription rate of the nucleic acid sequence (b) encoding the protein. All the above statements refer to that DNA strand which contains the nucleic acid sequence (b) encoding the protein (the coding strand) and not to the associated complementary DNA strand. Starting from the nucleic acid sequence (b) encoding the protein, the promoter sequence (a) is consequently preferably situated further upstream, i.e., in the 5' direction, on this DNA strand.

The nucleic acid sequence b) encodes the protein to be secreted. In this case, it is that protein which is to be prepared using an expression vector according to the invention (target protein).

The protein encoded by the nucleic acid sequence b) comprises a signal peptide having an amino acid sequence which is at least 80% identical to the amino acid sequence specified in SEQ ID NO: 2 or is at least 80% identical to the amino acid sequence specified in SEQ ID NO: 4 or is at least 80% identical to the amino acid sequence specified in SEQ ID NO: 6. It was found that such signal peptides bring about efficient secretion of the protein comprising them, more particularly recombinant protein. With increasing preference, the signal peptide comprises an amino acid sequence which is at least 81%, 82%, 83%, 84%, 85%, 86%, 87%, 88%, 89%, 90%, 91%, 92%, 93%, 94%, 95%, 96%, 97%, 98%, 99% and very particularly preferably 100% identical to the amino acid sequence specified in SEQ ID NO: 2, or is at least 81%, 82%, 83%, 84%, 85%, 86%, 87%, 88%, 89%, 90%, 91%, 92%, 93%, 94%, 95%, 96%, 97%, 98%, 99% and very particularly preferably 100% identical to the amino acid sequence specified in SEQ ID NO: 4, or is at least 81%, 82%, 83%, 84%, 85%, 86%, 87%, 88%, 89%, 90%, 91%, 92%, 93%, 94%, 95%, 96%, 97%, 98%, 99% and very particularly preferably 100% identical to the amino acid sequence specified in SEQ ID NO: 6. With particular preference, the signal peptide has an amino acid sequence which is at least 80%, 81%, 82%, 83%, 84%, 85%, 86%, 87%, 88%, 89%, 90%, 91%, 92%, 93%, 94%, 95%, 96%, 97%, 98%, 99% and very particularly preferably 100% identical to the amino acid sequence specified in SEQ ID NO: 2, or is at least 80%, 81%, 82%, 83%, 84%, 85%, 86%, 87%, 88%, 89%, 90%, 91%, 92%, 93%, 94%, 95%, 96%, 97%, 98%, 99% and very particularly preferably 100% identical to the amino acid sequence specified in SEQ ID NO: 4, or is at least 80%, 81%, 82%, 83%, 84%, 85%, 86%, 87%, 88%, 89%, 90%, 91%, 92%, 93%, 94%, 95%, 96%, 97%, 98%, 99% and very particularly preferably 100% identical to the amino acid sequence specified in SEQ ID NO: 6.

Very particular preference is given to the 100% identical sequences in each case, and so a correspondingly preferred expression vector is characterized in that the signal peptide encoded by the nucleic acid sequence b) has an amino acid sequence according to SEQ ID NO: 2, SEQ ID NO: 4 or SEQ ID NO: 6. Particularly preferred nucleic acid sequences encoding such signal peptides are specified in SEQ ID NO: 1, SEQ ID NO: 3 and SEQ ID NO: 5.

Instead of the aforementioned signal peptides which allow secretion of the protein, it is further possible to use sequences which are structurally homologous to these sequences. A structurally homologous sequence is understood to mean an amino acid sequence which has a succession of amino acids which exhibits spatial folding comparable to that of a signal peptide having the amino acid sequence according to SEQ ID NO: 2, SEQ ID NO: 4 or SEQ ID NO: 6. This spatial folding enables it to be recognized by the host cell as a secretory signal sequence and, consequently, the protein comprising the structurally homologous signal sequence to be transferred out of the host cell. Preferably, an interaction takes place with the translocation system used by the host cell. Therefore, the structurally homologous amino acid sequence binds preferably directly or indirectly to at least one component of the translocation system of the host cell. Direct binding is understood to mean a direct interaction, and indirect binding is understood to mean that the interaction can take place via one or more further components, more particularly proteins or other molecules, which act as adapters and, accordingly, function as a bridge between the structurally homologous amino acid sequence and a component of the translocation system of the host cell.

The identity of nucleic acid or amino acid sequences is determined by a sequence comparison. Such a comparison is achieved by assigning similar successions in the nucleotide sequences or amino acid sequences to one another. Said sequence comparison is preferably carried out on the basis of the BLAST algorithm, which is established in the prior art and commonly used (cf. for example Altschul, S. F., Gish, W., Miller, W., Myers, E. W. & Lipman, D. J. (1990) "Basic local alignment search tool." J. Mol. Biol. 215: 403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pages 3389-3402), and occurs principally by assigning similar successions of nucleotides or amino acids in the nucleic acid or amino acid sequences to one another. A tabular assignment of the positions in question is referred to as an alignment. A further algorithm available in the prior art is the FASTA algorithm. Sequence comparisons (alignments), more particularly multiple sequence comparisons, are usually created using computer programs. Frequently used are, for example, the Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs which are based on these programs or algorithms. For the purposes of the present invention, sequence comparisons and alignments are preferably created using the computer program Vector NTI® Suite 10.3 (Invitrogen Corporation, 1600 Faraday Avenue, Carlsbad, Calif., USA) using the predefined standard (default) parameters.

Such a comparison makes it possible to reveal the similarity of the compared sequences to one another. It is usually reported in percent identity, i.e., the proportion of identical nucleotides or amino acid residues on the same positions or positions corresponding to one another in an alignment. The broadened term of homology takes conserved amino acid substitutions into consideration in the case of amino acid sequences, i.e., amino acids having similar properties, because they usually exercise similar activities or functions within the protein. Therefore, the similarity of the compared sequences can also be reported as percent homology or percent similarity. Identity and/or homology values can be reported across entire polypeptides or genes or only across particular regions. Homologous or identical regions of different nucleic acid or amino acid sequences are therefore defined by congruities in the sequences. They often have the same or similar functions. They can be small and comprise only a few nucleotides or amino acids. Such small regions often exercise essential functions for the entire activity of the protein. It may therefore be advisable to base sequence congruities only on particular, possibly small regions. Unless otherwise indicated, identity or homology values in the present application refer, however, to the entire length of the various indicated nucleic acid or amino acid sequences.

The protein encoded by the nucleic acid sequence b) further comprises a further amino acid sequence. Said amino acid sequence is consequently the actual amino acid sequence of the protein without signal peptide. Preferably, the amino acid sequence is a mature protein. A mature protein is understood to mean the form thereof processed to completion, since it is possible that an associated gene encodes an immature form which, after translation, is additionally processed to give the mature form. For example, immature forms of the protein can comprise signal peptides and/or propeptides or elongations at the N-terminus and/or C-terminus which are no longer present in the mature form. For example, immature forms of proteases, more particularly subtilases and among these especially subtilisins, comprise a signal peptide and also a propeptide, which are no longer present in the mature form of the protease. Alternatively, the further amino acid sequence is the amino acid sequence of an immature protein which comprises a propeptide. Such an embodiment comes into consideration especially also for proteases, more particularly subtilases and among these especially subtilisins. In particularly preferred embodiments, the further amino acid sequence does not comprise a further signal peptide. In such embodiments according to the invention, only the signal peptide according to the invention consequently brings about the secretion of the protein from a host cell.

Particularly preferably, the further amino acid sequence of the protein comprises the amino acid sequence of an enzyme, more particularly a protease, amylase, cellulase, hemicellulase, mannanase, tannase, xylanase, xanthanase, xyloglucanase, β-glucosidase, a pectin-cleaving enzyme, carrageenase, perhydrolase, oxidase, oxidoreductase or a lipase, more particularly an enzyme as indicated below. Very particularly preferably, the further amino acid sequence of the protein comprises the amino acid sequence of a protease and this includes a subtilisin.

For example, one of the enzymes mentioned below can be advantageously prepared using an expression vector according to the invention.

Among the proteases, subtilisins are preferred. Examples thereof are the subtilisins BPN' and Carlsberg, the protease PB92, the subtilisins 147 and 309, the alkaline protease from *Bacillus lentus*, subtilisin DY and the enzymes which should be assigned to the subtilases, but no longer to the subtilisins in the narrower sense, these being thermitase, proteinase K and the proteases TW3 and TW7. Subtilisin Carlsberg is available in a further developed form under the trade name Alcalase® from Novozymes A/S, Bagsværd, Denmark. The subtilisins 147 and 309 are sold by Novozymes under the trade names Esperase®, or Savinase®. Derived from the DSM 5483 protease from *Bacillus lentus* are the protease variants known by the name BLAP®. Further preferred proteases are, furthermore, the enzymes known by the name PUR for example. Further proteases are, furthermore, the enzymes available under the trade names Durazym®, Relase®, Everlase®, Nafizym®, Natalase®, Kannase® and Ovozyme® from Novozymes, the enzymes available under the trade names Purafect®, Purafect® OxP, Purafect® Prime, Excellase® and Properase® from Genencor, the enzyme available under the trade name Protosol® from Advanced Biochemicals Ltd., Thane, India, the enzyme available under the trade name Wuxi® from Wuxi Snyder Bioproducts Ltd., China, the enzymes available under the trade names Proleather® and Protease P® from Amano Pharmaceuticals Ltd., Nagoya, Japan, and the enzyme available under the name Proteinase K-16 from Kao Corp., Tokyo, Japan. Also preferred are, furthermore, the proteases from *Bacillus gibsonii* and *Bacillus pumilus*, which are disclosed in the international patent applications WO2008/086916 and WO2007/131656.

Examples of amylases are the α-amylases from *Bacillus licheniformis*, from *Bacillus amyloliquefaciens* or from *Bacillus stearothermophilus* and, in particular, also the further developments thereof improved for use in washing agents or cleaning agents. The enzyme from *Bacillus licheniformis* is available from Novozymes under the name Termamyl® and from Danisco/Genencor under the name Purastar®ST. Products from further development of this α-amylase are available from Novozymes under the trade names Duramyl® and Termamyl®ultra, from Danisco/Genencor under the name Purastar®OxAm, and from Daiwa Seiko Inc., Tokyo, Japan, as Keistase®. The α-amylase of *Bacillus amyloliquefaciens* is sold by Novozymes under the name BAN®, and derived variants of the α-amylase from *Bacillus stearothermophilus* are likewise sold by Novozymes under the names BSG® and Novamyl®. Furthermore, the α-amylase from *Bacillus* sp. A 7-7 (DSM 12368) and the cyclodextrin glucanotransferase (CGTase) from *Bacillus agaradherens* (DSM 9948) should be mentioned. Similarly, fusion products of all the aforementioned molecules are usable. Moreover, the further developments of the α-amylase from *Aspergillus niger* and *A. oryzae* are suitable, said further developments being available under the trade names Fungamyl® from Novozymes. Further advantageous commercial products are, for example, the amylase Powerase® from Danisco/Genencor and the amylases Amylase-LT®, Stainzyme® and Stainzyme Plus®, the latter from Novozymes. Variants of these enzymes obtainable by point mutations can also be prepared according to the invention. Further preferred amylases are disclosed in the international published specifications WO 00/60060, WO 03/002711, WO 03/054177 and WO 07/079938, the disclosure of which is therefore expressly incorporated herein by reference and the relevant disclosure content of which is therefore expressly incorporated into the present patent application. Amylases to be prepared according to the invention are, furthermore, preferably α-amylases.

Examples of lipases or cutinases are the lipases originally available, or further developed, from *Humicola lanuginosa* (*Thermomyces lanuginosus*), more particularly those with the amino acid substitution D96L. They are sold, for example, by Novozymes under the trade names Lipolase®, Lipolase®Ultra, LipoPrime®, Lipozyme® and Lipex®. In addition, it is possible to prepare, for example, the cutinases which have been originally isolated from *Fusarium solani pisi* and *Humicola insolens*. From Danisco/Genencor, it is possible to prepare, for example, the lipases or cutinases whose starting enzymes have been originally isolated from *Pseudomonas mendocina* and *Fusarium solanii*. Further important commercial products which should be mentioned are the preparations M1 Lipase® and Lipomax® originally sold by Gist-Brocades (now Danisco/Genencor) and the enzymes sold by Meito Sangyo KK, Japan, under the names Lipase MY-30®, Lipase OF® and Lipase PL®, and furthermore the product Lumafast® from Danisco/Genencor.

Examples of cellulases (endoglucanases, EG) comprise sequences of the fungal, endoglucanase(EG)-rich cellulase preparation, or the further developments thereof, which is supplied by Novozymes under the trade name Celluzyme®. The products Endolase® and Carezyme®, likewise available from Novozymes, are based on the 50 kD EG and the 43 kD EG, respectively, from *Humicola insolens* DSM 1800. Further commercial products of said company which can be prepared are Cellusoft®, Renozyme® and Celluclean®. It is additionally possible to prepare, for example, cellulases which are available from AB Enzymes, Finland, under the trade names Ecostone® and Biotouch® and which are at least partly based on the 20 kD EG from Melanocarpus. Further cellulases from AB Enzymes are Econase® and Ecopulp®. Further suitable cellulases are from *Bacillus* sp. CBS 670.93 and CBS 669.93, the one from *Bacillus* sp. CBS 670.93 being available from Danisco/Genencor under the trade name Puradax®. Further commercial products of Danisco/Genencor which can be prepared are "Genencor detergent cellulase L" and IndiAge®Neutra.

Variants of these enzymes obtainable by point mutations can also be prepared according to the invention. Particularly preferred cellulases are *Thielavia terrestris* cellulase variants which are disclosed in the international published specification WO 98/12307, cellulases from *Melanocarpus*, more particularly *Melanocarpus albomyces*, which are disclosed in the international published specification WO 97/14804, EGIII cellulases from *Trichoderma reesei* which are disclosed in the European patent application EP 1 305 432 or variants obtainable therefrom, more particularly those which are disclosed in the European patent applications EP 1240525 and EP 1305432, and also cellulases which are disclosed in the international published specifications WO 1992006165, WO 96/29397 and WO 02/099091. The respective disclosures thereof are therefore expressly incorporated herein by reference and the relevant disclosure content thereof is therefore expressly incorporated into the present patent application.

Furthermore, it is possible to prepare further enzymes which are covered by the term hemicellulases. These include, for example, mannanases, xanthan lyases, xanthanases, xyloglucanases, xylanases, pullulanases, pectin-cleaving enzymes and β-glucanases. The β-glucanase obtained from *Bacillus subtilis* is available under the name Cereflo® from Novozymes. Hemicellulases particularly preferred according to the invention are mannanases, which are sold, for example, under the trade names Mannaway® from Novozymes or Purabrite® from Genencor. For the purposes of the present invention, the pectin-cleaving enzymes likewise include enzymes having the names pectinase, pectate lyase, pectinesterase, pectin demethoxylase, pectin methoxylase, pectin methylesterase, pectase, pectin methylesterase, pectinoesterase, pectin pectylhydrolase, pectin depolymerase, endopolygalacturonase, pectolase, pectin hydrolase, pectin polygalacturonase, endopolygalacturonase, poly-α-1,4-galacturonide glycanohydrolase, endogalacturonase, endo-D-galacturonase, galacturan 1,4-α-galacturonidase, exopolygalacturonase, polygalacturonate hydrolase, exo-D-galacturonase, exo-D-galacturonanase, exopoly-D-galacturonase, exo-poly-α-galacturonosidase, exopolygalacturonosidase or exopolygalacturanosidase. Examples of enzymes suitable in this regard are, for example, available under the names Gamanase®, Pektinex AR®, X-Pect® or Pectaway® from Novozymes, under the name Rohapect UF®, Rohapect Rohapect PTE100®, Rohapect MPE®, Rohapect MA plus HC, Rohapect DA12L®, Rohapect 10L®, Rohapect B1L® from AB Enzymes, and under the name Pyrolase® from Diversa Corp., San Diego, Calif., USA.

Furthermore, it is also possible to prepare oxidoreductases, for example oxidases, oxygenases, catalases, peroxidases, such as haloperoxidases, chloroperoxidases, bromoperoxidases, lignin peroxidases, glucose peroxidases or manganese peroxidases, dioxygenases or laccases (phenol oxidases, polyphenol oxidases). Suitable commercial products which should be mentioned are Denilite® 1 and 2 from Novozymes. Further enzymes are disclosed in the international patent applications WO 98/45398, WO 2005/056782, WO 2004/058961 and WO 2005/124012.

In a further embodiment of the invention, the further amino acid sequence is not naturally present together with the signal peptide in a polypeptide chain in a microorganism. Consequently, the protein encoded by the nucleic acid sequence b) is a recombinant protein. Not naturally present means, therefore, that the two amino acid sequences are not constituents of an endogenous protein of the microorganism. A protein comprising the signal peptide and the further amino acid sequence consequently cannot be expressed in the microorganism by a nucleic acid sequence which is part of the chromosomal DNA of the microorganism in its wild-type form. Such a protein and/or the nucleic acid sequence encoding it in each case is consequently not present in the wild-type form of the microorganism and/or cannot be isolated from the wild-type form of the microorganism. Both sequences—signal peptide and further amino acid sequence—must therefore be assigned to two different polypeptide chains in a wild-type form of a microorganism, if both are, or may be, present at all in the wild-type form of a microorganism. In the context of this embodiment of the invention, signal peptide and further amino acid sequence, or the nucleic acids encoding them, were therefore newly combined using gene-technology methods, and this combination of signal peptide and further amino acid sequence does not exist in nature. In the wild-type form of a microorganism, such a linkage of the signal peptide with the further amino acid sequence is consequently not present, specifically neither on the DNA level nor on the protein level. However, the signal peptide and the further amino acid sequence, or the nucleic acid sequences encoding them both, can both be of natural origin, but the combination thereof does not exist in nature. Signal peptide and further amino acid sequence themselves can, however, originate from the same microorganism or else from different microorganisms.

In a preferred embodiment, a nucleic acid according to the invention is characterized in that it is a nonnatural nucleic acid. Nonnatural means that a nucleic acid according to the invention cannot be isolated from an organism in its wild-type form that occurs in nature. More particularly and with regard to wild-type bacteria, a nucleic acid according to the invention is therefore not a nucleic acid endogenous to bacteria.

Preferably, the sequences (a) and (b) do not originate from the same organism(s), more particularly bacteria, but instead originate from different organisms, more particularly bacteria. Different bacteria are, for example, bacteria which belong to different strains or species or genera.

In a further embodiment of the invention, the expression vector is characterized in that the signal peptide is arranged N-terminal to the further amino acid sequence in the protein encoded by the nucleic acid sequence b). The protein encoded by the nucleic acid sequence b) therefore has the following structure: N-terminus—signal peptide—(optional additional amino acid sequence)—further amino acid sequence—C-terminus. Such a structure of the protein to be expressed has been found to be particularly advantageous.

In a further embodiment of the invention, the expression vector is characterized in that the protein encoded by the nucleic acid sequence b) further comprises a connecting sequence arranged between the signal peptide and the further amino acid sequence of the protein. The protein encoded by the nucleic acid sequence b) therefore has the following structure: N-terminus—signal peptide—connecting sequence (also "coupler" or "spacer")—further amino acid sequence—C-terminus. Such a structure of the protein to be expressed has likewise been found to be particularly advantageous. Preferably, the length of the connecting sequence is between 1 and 50 amino acids, between 2 and 25 amino acids, between 2 and 15 amino acids, between 3 and 10 amino acids, and particularly preferably between 3 and 5 amino acids. An example of a particularly preferred connecting sequence is the succession of amino acids of alanine, glutamic acid and phenylalanine (from the N-terminus to the C-terminus).

In a further embodiment of the invention, the expression vector is characterized in that the further amino acid sequence of the protein comprises the amino acid sequence of a protease, said amino acid sequence of the protease being at least 80% identical to SEQ ID NO: 7. Preferably, the amino acid sequence of the protease is at least 81%, 82%, 83%, 84%, 85%, 86%, 87%, 88%, 89%, 90%, 91%, 92%, 93%, 94%, 95%, 96%, 97%, 98%, 99% and very particularly preferably 100% identical to SEQ ID NO: 7.

Alternatively, the further amino acid sequence of the protein comprises the amino acid sequence of a protease which is at least 80% identical to SEQ ID NO: 8. Preferably, the amino acid sequence of the protease is at least 81%, 82%, 83%, 84%, 85%, 86%, 87%, 88%, 89%, 90%, 91%, 92%, 93%, 94%, 95%, 96%, 97%, 98%, 99% and very particularly preferably 100% identical to SEQ ID NO: 8.

Alternatively, the further amino acid sequence of the protein comprises the amino acid sequence of a protease which is at least 80% identical to SEQ ID NO: 9. Preferably, the amino acid sequence of the protease is at least 81%, 82%, 83%, 84%, 85%, 86%, 87%, 88%, 89%, 90%, 91%, 92%, 93%, 94%, 95%, 96%, 97%, 98%, 99% and very particularly preferably 100% identical to SEQ ID NO: 9.

Alternatively, the further amino acid sequence of the protein comprises the amino acid sequence of a protease which is at least 80% identical to SEQ ID NO: 10 and has the amino acid glutamic acid (E) or aspartic acid (D) at position 99 in the numbering according to SEQ ID NO: 10. Preferably, the amino acid sequence of the protease is at least 81%, 82%, 83%, 84%, 85%, 86%, 87%, 88%, 89%, 90%, 91%, 92%, 93%, 94%, 95%, 96%, 97%, 98%, 99% identical and very particularly preferably identical to SEQ ID NO: 10 in positions 1 to 98 and 100 to 269 in the numbering according to SEQ ID NO: 10.

Alternatively, the further amino acid sequence of the protein comprises the amino acid sequence of a protease which is at least 80% identical to SEQ ID NO: 10 and has the amino acid glutamic acid (E) or aspartic acid (D) at position 99 in the numbering according to SEQ ID NO: 10 and has, furthermore, at least one of the following amino acids in the numbering according to SEQ ID NO: 10:
(a) threonine at position 3 (3T),
(b) isoleucine at position 4 (4I),
(c) alanine, threonine or arginine at position 61 (61A, 61T or 61R),
(d) aspartic acid or glutamic acid at position 154 (154D or 154E),
(e) proline at position 188 (188P),
(f) methionine at position 193 (193M),
(g) isoleucine at position 199 (199I),
(h) aspartic acid, glutamic acid or glycine at position 211 (211 D, 211E or 211G),
(i) combinations of the amino acids (a) to (h).

Preferably, the amino acid sequence of this protease is at least 81%, 82%, 83%, 84%, 85%, 86%, 87%, 88%, 89%, 90%, 91%, 92%, 93%, 94%, 95%, 96%, 97%, 98%, 99% identical and very particularly preferably identical to SEQ ID NO: 10 in all positions which are not modified or not intended for modification. Very particularly preferably, the further amino acid sequence of the protein therefore comprises the amino acid sequence of a protease which has an amino acid sequence modified in at least two positions with respect to SEQ ID NO: 10, with the first modification being glutamic acid at position 99 in the numbering according to SEQ ID NO: 10 and the second modification, in the numbering according to SEQ ID NO: 10, being selected from the group consisting of:
(a) threonine at position 3 (3T),
(b) isoleucine at position 4 (4I),
(c) alanine, threonine or arginine at position 61 (61A, 61T or 61R),
(d) aspartic acid or glutamic acid at position 154 (154D or 154E),
(e) proline at position 188 (188P),
(f) methionine at position 193 (193M),
(g) isoleucine at position 199 (199I),
(h) aspartic acid, glutamic acid or glycine at position 211 (211 D, 211E or 211G),
(i) combinations of the amino acids (a) to (h).

Likewise very particularly preferably, the further amino acid sequence of the protein comprises the amino acid sequence of a protease which has an amino acid sequence modified in at least two positions with respect to SEQ ID NO: 10, with the first modification being aspartic acid at position 99 in the numbering according to SEQ ID NO: 10 and the second modification, in the numbering according to SEQ ID NO: 10, being selected from the group consisting of:
(a) threonine at position 3 (3T),
(b) isoleucine at position 4 (4I),
(c) alanine, threonine or arginine at position 61 (61A, 61T or 61R),
(d) aspartic acid or glutamic acid at position 154 (154D or 154E),
(e) proline at position 188 (188P),
(f) methionine at position 193 (193M),
(g) isoleucine at position 199 (199I),
(h) aspartic acid, glutamic acid or glycine at position 211 (211 D, 211E or 211G),
(i) combinations of the amino acids (a) to (h).

It was found that the above-mentioned proteases can also be prepared particularly advantageously using expression vectors according to the invention. For such embodiments of the invention, it was found that such combinations of signal peptides and subtilisins make it possible to achieve particularly good product yields in a fermentation procedure. Specified in this regard are the amino acid sequences of the mature proteases, i.e., the products processed to completion. In an expression vector according to the invention, it is also possible in this regard to include further sequences of the immature protease, more particularly propeptides for example. In such a case, the further amino acid sequence of the protein comprises the amino acid sequence of the protease and of the propeptide. A further embodiment of the invention is consequently characterized in that the further amino acid sequence of the protein comprises the amino acid sequence of a protease, more particularly a protease as described above, together with a propeptide or its propeptide.

In general, the further amino acid sequence of the protein need not merely comprise the amino acid sequence of a mature protein; on the contrary, it is possible to include further amino acid sequences such as, for example, propeptides of said amino acid sequence. This applies not only to proteases, but also to all proteins, more particularly all other types of enzymes.

Nucleic acids and expression vectors according to the invention can be generated via methods known per se for modifying nucleic acids. Such methods are, for example, presented in relevant manuals such as the one by Fritsch, Sambrook and Maniatis, "Molecular cloning: a laboratory manual", Cold Spring Harbor Laboratory Press, New York, 1989, and familiar to a person skilled in the art in the field of biotechnology. Examples of such methods are chemical synthesis or the polymerase chain reaction (PCR), optionally in conjunction with further standard methods in molecular biology and/or chemistry or biochemistry.

Nonhuman host cells containing vectors according to the invention, preparations methods in which corresponding host cells are used, and the uses of corresponding vectors or host cells are associated with all aforementioned inventive subject matter and embodiments as further inventive subject matter. Therefore, the above statements relate correspondingly to said inventive subject matter.

The invention further provides a nonhuman host cell containing an expression vector according to the invention. An expression vector according to the invention is preferably introduced into the host cell by the transformation thereof. According to the invention, this is preferably carried out by transforming a vector according to the invention into a microorganism, which then constitutes a host cell according to the invention. Alternatively, it is also possible for individual components, i.e., nucleic acid portions or fragments, for example the components (a) and/or (b), of a vector according to the invention to be introduced into a host cell in such a way that the thus resulting host cell comprises a vector according to the invention. This approach is especially suitable if the host cell already comprises one or more constituents of a vector according to the invention and the further constituents are then complemented accordingly. Methods for transforming cells are established in the prior art and well known to a person skilled in the art. In principle, all cells, i.e., prokaryotic or eukaryotic cells, are suitable as host cells. Host cells which can be advantageously manipulated genetically, for example with regard to transformation with the vector and the stable establishment thereof, are preferred, for example unicellular fungi or bacteria. In addition, preferred host cells are easily manipulatable from a microbiological and biotechnological perspective. This concerns, for example, ease of culture, high growth rates, low demands on fermentation media, and good production and secretion rates for foreign proteins. In many cases, it is necessary to determine experimentally the optimal expression systems for each individual case from the abundance of different systems available in the prior art.

Further preferred embodiments are host cells which are regulatable in terms of their activity owing to genetic regulatory elements which, for example, are made available on the vector, but may also be present in said cells from the start. For example, they can be stimulated to express by controlled addition of chemical compounds serving as activators, by changing the culture conditions, or upon attainment of a particular cell density. This allows economical production of the proteins.

Preferred host cells are prokaryotic or bacterial cells. Bacteria have short generation times and low demands in terms of culture conditions. As a result, it is possible to establish cost-effective methods. In addition, a wealth of experience is available to a person skilled in the art in the case of bacteria in fermentation technology. For a specific production process, Gram-negative or Gram-positive bacteria may be suitable for a very wide variety of different reasons which are to be determined experimentally on an individual basis, such as nutrient sources, rate of product formation, time requirement, etc.

In the case of Gram-negative bacteria, for example *Escherichia coli*, a multiplicity of polypeptides are secreted into the periplasmic space, i.e., into the compartment between the two membranes encasing the cells. This may be advantageous for specific applications. Furthermore, it is also possible to configure Gram-negative bacteria in such a way that they eject the expressed polypeptides not only into the periplasmic space, but also into the medium surrounding the bacterium. By contrast, Gram-positive bacteria, for example *Bacilli* or *Actinomycetaceae* or other representatives of the *Actinomycetales*, do not have an outer membrane, and so secreted proteins are immediately released into the medium surrounding the bacteria, generally the culture medium, from which the expressed polypeptides can be purified. They can be isolated directly from the medium or processed further. In addition, Gram-positive bacteria are related or identical to most organisms of origin for technically important enzymes and usually themselves form comparable enzymes, and so they have similar codon usage and their protein-synthesis apparatus is naturally organized accordingly.

Codon usage is understood to mean the rendering of the genetic code into amino acids, i.e., which nucleotide order (triplet or base triplet) encodes which amino acid or which function, for example the start and end of the region to be translated, binding sites for various proteins, etc. Thus, each organism, more particularly each production strain, has a particular codon usage. Bottlenecks can occur in protein biosynthesis if the codons on the transgenic nucleic acid in the host cell are faced with a comparatively low number of loaded tRNAs. By contrast, synonymous codons encode the same amino acids and can be translated more efficiently depending on the host. This optionally necessary transcription thus depends on the choice of expression system. Especially in the case of samples composed of unknown, possibly unculturable organisms, a corresponding adaptation may be necessary.

The present invention is, in principle, applicable to all microorganisms, more particularly all fermentable microorganisms, particularly preferably those of the genus *Bacillus*, and results in it being possible to realize, through the use of such microorganisms as production organisms, an increased product yield in a fermentation procedure. Such microorganisms are preferred host cells for the purposes of the invention.

In a further embodiment of the invention, the host cell is therefore characterized in that it is a bacterium, preferably one selected from the group of the genera of *Escherichia, Klebsiella, Bacillus, Staphylococcus, Corynebacterium, Arthrobacter, Streptomyces, Stenotrophomonas* and *Pseudomonas*, more preferably one selected from the group of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor* and *Stenotrophomonas maltophilia*. Very particular preference is given to *Bacillus licheniformis*.

However, the host cell may also be a eukaryotic cell, characterized in that it has a nucleus. The invention therefore further provides a host cell, characterized in that it has a nucleus.

In contrast to prokaryotic cells, eukaryotic cells are capable of posttranslationally modifying the protein formed. Examples thereof are fungi such as *Actinomycetaceae* or yeasts such as *Saccharomyces* or *Kluyveromyces*. This may be particularly advantageous when, for example, the proteins are to undergo, in conjunction with their synthesis, specific modifications, which is allowed by such systems. Modifications which eukaryotic systems carry out especially in conjunction with protein synthesis include, for example, the binding of low-molecular-weight compounds such as membrane anchors or oligosaccharides. Such oligosaccharide modifications may, for example, be desirable for lowering the allergenicity of an expressed protein. Coexpression with the enzymes naturally formed by such cells, for example cellulases, may also be advantageous. Furthermore, thermophilic fungal expression systems may, for example, be especially suitable for the expression of temperature-resistant variants.

For the purposes of the invention, proteins encoded by the nucleic acid sequence (b), more particularly those as described above, are considered to be the products formed during fermentation. They are therefore preferably enzymes, particularly preferably proteases, and very particularly preferably subtilisins.

Furthermore, the host cells can be modified with respect to their requirements in terms of culture conditions, can have other or additional selection markers, or can express other or additional proteins. More particularly, the host cells can be those which express multiple proteins or enzymes. Preferably, they secrete them into the medium surrounding the host cells.

The host cells according to the invention are cultured and fermented in a manner known per se, for example in batch systems or continuous systems. In the first case, an appropriate culture medium is inoculated with the host cells and the product harvested from the medium after a period to be determined experimentally. Continuous fermentation procedures involve attaining a steady state in which, over a comparatively long period, cells partly die but also grow again and product can be removed at the same time from the medium.

Host cells according to the invention are preferably used to prepare proteins encoded by the nucleic acid sequence (b). The invention therefore further provides a method for preparing a protein, comprising a) culturing a host cell according to the invention b) isolating the protein from the culture medium or from the host cell.

This inventive subject matter preferably comprises fermentation methods. Fermentation methods are known per se from the prior art and constitute the actual industrial-scale production step, generally followed by an appropriate purification method for the product prepared, for example the protein. All fermentation methods involving a corresponding method for preparing a protein constitute embodiments of this inventive subject matter.

In this connection, the various optimal conditions for the preparation methods, more particularly the optimal culture conditions for the host cells used, must be determined experimentally according to the knowledge of a person skilled in the art, for example with respect to fermentation volume and/or media composition and/or oxygen supply and/or stirrer speed.

Fermentation methods characterized in that the fermentation is carried out via a continuous supply strategy are one particular possibility. In this case, the media constituents which are consumed by the ongoing culture are continuously fed; this is also known as a continuous feed strategy. As a result, considerable increases both in the cell density and in the cell mass or dry mass and/or especially the activity of the protein of interest, preferably an enzyme, can be attained.

Furthermore, the fermentation can also be configured in such a way that unwanted metabolic products are filtered out or neutralized by addition of buffer or of counterions appropriate in each case.

The prepared protein can be harvested from the fermentation medium. Such a fermentation method is advantageous over isolation of the polypeptide from the host cell, i.e., product processing from the cell mass (dry mass). According to the invention, secretion markers suitable in this regard are provided with the signal peptides.

All facts explained above can be combined to form methods for preparing proteins. In this regard, a multiplicity of possible combinations of method steps is conceivable. The optimal method must be determined for each specific individual case.

The invention further provides for the use of an expression vector according to the invention or of a host cell according to the invention for preparing a protein.

All facts, subject matter and embodiments which are already described above are also applicable to this inventive subject matter. Therefore, reference is expressly made at this point to the disclosure at the corresponding point with the indication that said disclosure also applies to the uses according to the invention (use of the vector or of the host cell).

EXAMPLES

All molecular biology work steps follow standard methods, as specified, for example, in the manual from Fritsch, Sambrook and Maniatis "Molecular cloning: a laboratory manual", Cold Spring Harbor Laboratory Press, New York, 1989, or comparable relevant works. Enzymes and kits were used according to the instructions from the respective manufacturers.

Example 1: Preparation of Expression Vectors According to the Invention

The plasmid pBSMuL3 (Brockmeier et al., 2006) was shortened by SacI restriction digestion and subsequent religation around the *E. coli* portion. The resulting plasmid, pBSMuL5 (cf. FIG. 1), was used as a vector for cloning the proteases including propeptide into the EcoRI and BamHI restriction sites. To this end, amplification was carried out of the genes of the protease according to SEQ ID NO: 8 with the primers according to SEQ ID NO: 11 and SEQ ID NO: 12, and of the alkaline protease according to SEQ ID NO: 9 with the primers according to SEQ ID NO: 13 and SEQ ID NO: 14. The resulting plasmids were used as vectors for cloning the signal peptides into the HindIII and EcoRI restriction sites. The DNA fragment of the control signal peptide SubC (*B. licheniformis*, NCBI (National Center for Biotechnology Information) accession number: X91260.1), as benchmark, was amplified using the primers according to SEQ ID NO: 15 and SEQ ID NO: 16 and cloned in each case into the HindIII and EcoRI restriction sites of the plasmids, producing plasmids having a nucleic acid sequence b) encoding a protein having the signal peptide SubC in conjunction with a protease according to SEQ ID NO: 8 (plasmid 1) or SEQ ID NO: 9 (plasmid 2). These plasmids were subsequently used as control or benchmark. The DNA fragment of the signal peptide according to SEQ ID NO: 2 was amplified using the primers according to SEQ ID NO: 19 and SEQ ID NO: 20, the DNA fragment of the signal peptide according to SEQ ID NO: 4 was amplified with the primers according to SEQ ID NO: 17 and SEQ ID NO: 18, and the DNA fragment of the signal peptide according to SEQ ID NO: 6 was amplified with the primers according to SEQ ID NO: 21 and SEQ ID NO: 22. Whereas the DNA fragments of the signal peptides according to SEQ ID NO: 2 and 4 were each cloned into the vector encoding a protease according to SEQ ID NO: 8 (plasmids 3 and 4), the DNA fragment of the signal peptide according to SEQ ID NO: 6 was inserted into the vector encoding a protease according to SEQ ID NO: 9 (plasmid 5). Associated with the cloning, a sequence of 9 nucleotides encoding the succession of amino acids AEF (cf. FIG. 1) was introduced between the DNA sequence of the particular signal peptide and the DNA sequence of the propeptide of the particular protease. This so-called connecting sequence contains the recognition sequence of the restriction endonuclease EcoRI.

All oligonucleotides used as primers are listed in table 1 below:

TABLE 1

| Name | Nucleotide sequence (in 5'→3' orientation; the restriction sites are underlined) | Restriction site |
|---|---|---|
| SEQ ID NO: 11 | ATAT<u>GAATTC</u>GCTGAGGAAGCAAAAGAAAA | EcoRI |
| SEQ ID NO: 12 | ATAT<u>GGATCC</u>TTAGCGTGTTGCCGCTTCTGC | BamHI |
| SEQ ID NO: 13 | ATAT<u>GAATTC</u>GCTGAGGAAGCAAAAGAAAA | EcoRI |

TABLE 1-continued

| Name | Nucleotide sequence (in 5'→3' orientation; the restriction sites are underlined) | Restriction site |
|---|---|---|
| SEQ ID NO: 14 | ATAT<u>GGATCC</u>TTAGCGCGTTGCTGCATCTGC | BamHI |
| SEQ ID NO: 15 | ATAT<u>AAGCTT</u>AAGGAGGATATTATGATGAGGAAAAAGAGTTTT | HindIII |
| SEQ ID NO: 16 | ATAT<u>GAATTC</u>AGCTGCAGAAGCGGAATCGCTGAA | EcoRI |
| SEQ ID NO: 17 | ATAT<u>AAGCTT</u>AAGGAGGATATTATGAAAAAACTATTCAAAACC | HindIII |
| SEQ ID NO: 18 | ATAT<u>GAATTC</u>AGCAGCCGCCGCAGATTGTGAGAA | EcoRI |
| SEQ ID NO: 19 | ATAT<u>AAGCTT</u>AAGGAGGATATTATGGCGAAACCACTATCAAAA | HindIII |
| SEQ ID NO: 20 | ATAT<u>GAATTC</u>AGCAGCGTCTGCCGCGGGTAAACC | EcoRI |
| SEQ ID NO: 21 | ATAT<u>AAGCTT</u>AAGGAGGATATTATGACATTGACTAAACTGAAA | HindIII |
| SEQ ID NO: 22 | ATAT<u>GAATTC</u>AGCGGCAAGTGCCTGACTGGAAAA | EcoRI |

Example 2: Expression of the Proteins

A *Bacillus licheniformis* strain was transformed with the plasmids 1 to 5 to obtain the various protease production strains. For the inoculation of cultures, use was made of single colonies from agar plates which were incubated overnight (ON). For the quantitative determination of the efficiency of secretion, the single colonies were transferred directly from the agar plates to deep-well MTPs (microtiter plates; 96 wells each containing 1 mL of selective LB medium). In said determination, each single colony was transferred to at least two wells in parallel in order to obtain duplicate or triplicate determination as a result of the multiple cultivation of the particular clone. For the inoculation of the deep-well MTPs, only clones which were incubated overnight at 37° C. were used. After cultivation for 20 h at 37° C. in the microtiter plate shaker (Timix 5 from Edmund-Bühler, Hechingen), all clones were replicated on LB agar plates and subsequently the cells were sedimented by centrifugation (4000 rpm, 20 min, 4° C.). All pipetting steps which follow were carried out using multichannel pipets (Eppendorf, Hamburg), with the use of the reverse-pipetting mode and no volumes smaller than 15 µl being pipetted. In each case, the smallest volume was initially charged in the MTP and the larger volumes were added thereto and the MTP was mixed at each dilution step for 10 seconds in the spectrophotometer "Spectramax 250" (Molecular Devices, Sunnyvale, USA). For the generation of the corresponding dilutions, the culture supernatant was removed using the multichannel pipet and transferred to microtiter plates (96 wells, F-bottom, transparent, from Greiner Bio-One, Frickenhausen).

Subsequently, the proteolytic activity in the culture supernatants or dilutions was determined via the release of the chromophore para-nitroaniline (pNA) from the substrate suc-L-Ala-L-Ala-L-Pro-L-Phe-p-nitroanilide (suc-AAPF-pNA). The protease cleaves the substrate and releases pNA. The release of the pNA causes an increase in the absorbance at 410 nm, its change in time being a measure of the enzymatic activity (cf. Del Mar et al., Anal. Biochem., 99: 316-320, 1979).

For the determination of the efficiency of secretion of the various strains, an internal control construct (plasmid 1 or plasmid 2) was concomitantly cultivated in each MTP cultivation. The proteolytic activity of the strain having the control construct, as determined in the culture supernatant, was defined as 100%.

Compared with the control which comprised the plasmid 1, the strains containing the plasmids 3 and 4 according to the invention attained a protease activity which was increased by 194%+/−48 and 230%+/−38, respectively (cf. FIG. 2).

Compared with the control which comprised the plasmid 2, the strain containing the plasmid 5 according to the invention attained a protease activity which was increased by 44%+/−10 (cf. FIG. 3).

SEQUENCE LISTING

<160> NUMBER OF SEQ ID NOS: 22

Figure 1:
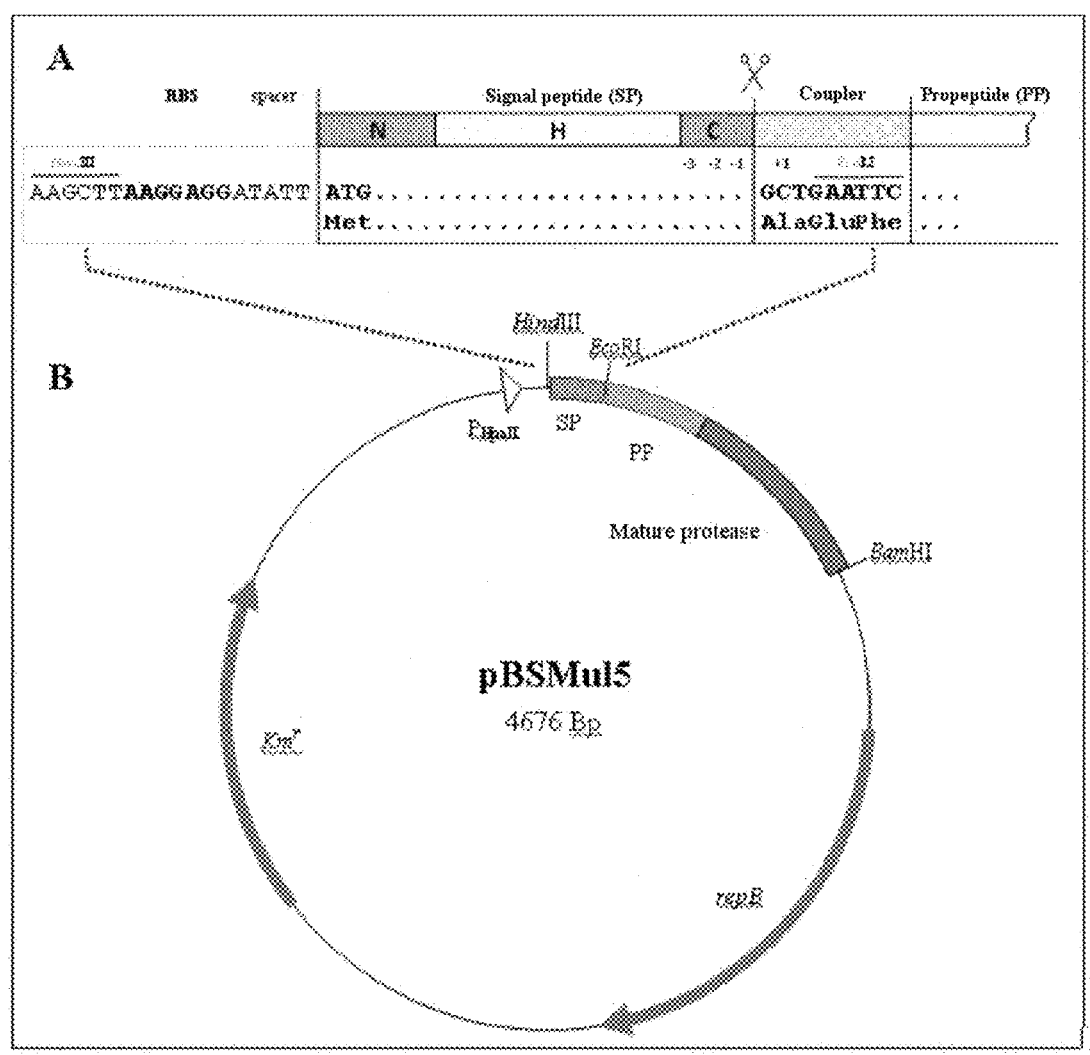
FIG. 1: Diagram of the cloning strategy in the *Bacillus* expression vector pBSMul5 (modified from Brockmeier et al., 2006). (A) The DNA fragments of the signal peptides were amplified at the N-terminus with a Hindil restriction site, a standardized ribosome binding site (RBS), followed by a spacer region and the standardized start codon for methionine. A coupler having an alanine at the "+1" position and the EcoRI restriction site was attached between signal peptide and N-terminus of the protease to be secreted. (B) *Bacillus* vector pBSMul5 having the HpaII promoter, the particular secretion target (cloned via EcoRI and BamHI), and the kanamycin-resistance cassette and the replication protein repB for *Bacillus*.
Figure 2:
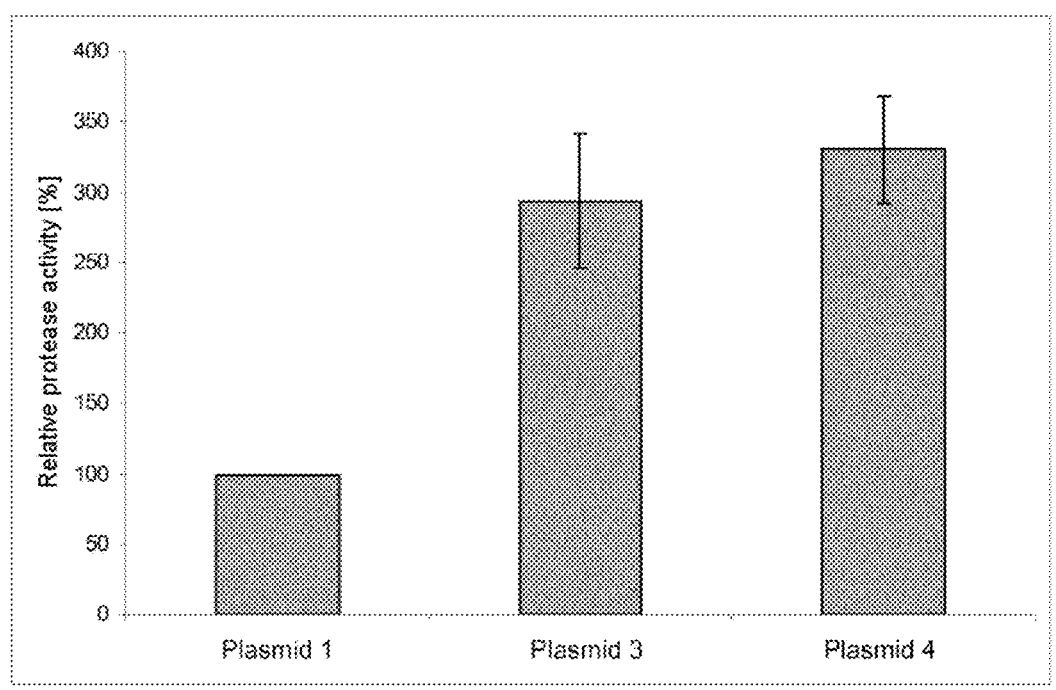
FIG. 2: Relative protease activity in the culture supernatant of *Bacillus licheniformis* containing the protease according to SEQ ID NO: 8 and three different signal peptides in pBSMul5. The proteolytic activity of the construct plasmid 1 was defined as 100% (control). The values were determined in at least two independent cultivations. The error bars indicate the standard deviation.
Figure 3:
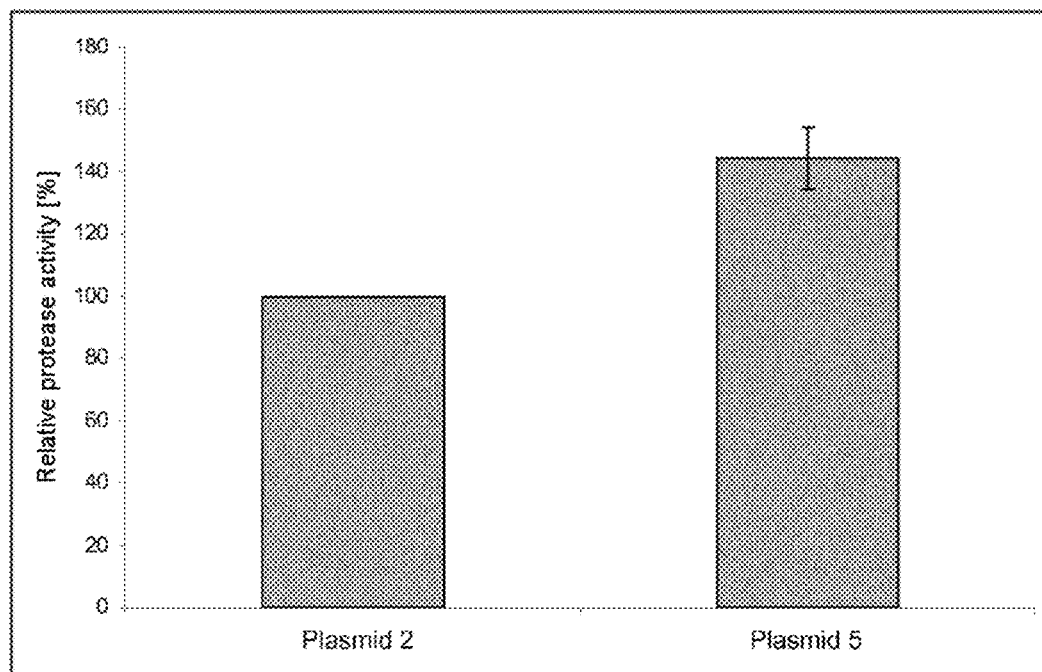
FIG. 3: Relative protease activity in the culture supernatant of *Bacillus licheniformis* containing the protease according to SEQ ID NO: 9 and two different signal peptides in pBSMul5. The proteolytic activity of the construct plasmid 2 was defined as 100% (control). The values were determined in at least two independent cultivations. The error bars indicate the standard deviation.

<210> SEQ ID NO 1
<211> LENGTH: 126
<212> TYPE: DNA
<213> ORGANISM: Bacillus subtilis
<220> FEATURE:
<221> NAME/KEY: CDS
<222> LOCATION: (1)..(126)

<400> SEQUENCE: 1

```
atg gcg aaa cca cta tca aaa ggg gga att ttg gtg aaa aaa gta ttg      48
Met Ala Lys Pro Leu Ser Lys Gly Gly Ile Leu Val Lys Lys Val Leu
1               5                   10                  15 att gca ggt gca gta gga aca gca gtt ctt ttc gga acc ctt tca tca      96
Ile Ala Gly Ala Val Gly Thr Ala Val Leu Phe Gly Thr Leu Ser Ser
                20                  25                  30 ggt ata cca ggt tta ccc gcg gca gac gct                             126
Gly Ile Pro Gly Leu Pro Ala Ala Asp Ala
                35                  40
```

<210> SEQ ID NO 2
<211> LENGTH: 42
<212> TYPE: PRT
<213> ORGANISM: Bacillus subtilis

<400> SEQUENCE: 2

```
Met Ala Lys Pro Leu Ser Lys Gly Gly Ile Leu Val Lys Lys Val Leu
1               5                   10                  15

Ile Ala Gly Ala Val Gly Thr Ala Val Leu Phe Gly Thr Leu Ser Ser
                20                  25                  30

Gly Ile Pro Gly Leu Pro Ala Ala Asp Ala
                35                  40
```

<210> SEQ ID NO 3
<211> LENGTH: 81
<212> TYPE: DNA
<213> ORGANISM: Bacillus licheniformis
<220> FEATURE:
<221> NAME/KEY: CDS
<222> LOCATION: (1)..(81)

<400> SEQUENCE: 3

```
atg aaa aaa cta ttc aaa acc att gtt aca ctg tca ctc ttg att tct      48
Met Lys Lys Leu Phe Lys Thr Ile Val Thr Leu Ser Leu Leu Ile Ser
1               5                   10                  15 gga acg ctt tta ttc tca caa tct gcg gcg gct                          81
Gly Thr Leu Leu Phe Ser Gln Ser Ala Ala Ala
                20                  25
```

<210> SEQ ID NO 4
<211> LENGTH: 27
<212> TYPE: PRT
<213> ORGANISM: Bacillus licheniformis

<400> SEQUENCE: 4

```
Met Lys Lys Leu Phe Lys Thr Ile Val Thr Leu Ser Leu Leu Ile Ser
1               5                   10                  15

Gly Thr Leu Leu Phe Ser Gln Ser Ala Ala Ala
                20                  25
```

<210> SEQ ID NO 5
<211> LENGTH: 84
<212> TYPE: DNA

```
<213> ORGANISM: Bacillus subtilis
<220> FEATURE:
<221> NAME/KEY: CDS
<222> LOCATION: (1)..(84)

<400> SEQUENCE: 5 atg aca ttg act aaa ctg aaa atg ctg agt atg tta acc gtg atg att    48
Met Thr Leu Thr Lys Leu Lys Met Leu Ser Met Leu Thr Val Met Ile
1               5                   10                  15 gca tct tta ttc att ttt tcc agt cag gca ctt gcc                    84
Ala Ser Leu Phe Ile Phe Ser Ser Gln Ala Leu Ala
            20                  25

<210> SEQ ID NO 6
<211> LENGTH: 28
<212> TYPE: PRT
<213> ORGANISM: Bacillus subtilis

<400> SEQUENCE: 6

Met Thr Leu Thr Lys Leu Lys Met Leu Ser Met Leu Thr Val Met Ile
1               5                   10                  15

Ala Ser Leu Phe Ile Phe Ser Ser Gln Ala Leu Ala
            20                  25

<210> SEQ ID NO 7
<211> LENGTH: 269
<212> TYPE: PRT
<213> ORGANISM: Bacillus lentus

<400> SEQUENCE: 7

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220
```

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

<210> SEQ ID NO 8
<211> LENGTH: 269
<212> TYPE: PRT
<213> ORGANISM: Bacillus lentus

<400> SEQUENCE: 8

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Met Ala Pro Gly Val Asn Ile Gln Ser Thr Tyr Pro Gly Ser Thr Tyr
        195                 200                 205

Ala Ser Asp Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 9
<211> LENGTH: 269
<212> TYPE: PRT
<213> ORGANISM: Bacillus gibsonii

<400> SEQUENCE: 9

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
                20                  25                  30

Thr Gly Ile Ala Gln His Ser Asp Leu Thr Ile Arg Gly Gly Ala Ser
            35                  40                  45

Phe Val Pro Gly Glu Ser Thr Thr Ala Asp Leu Asn Gly His Gly Thr
        50                  55                  60

His Val Ala Gly Thr Val Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 10
<211> LENGTH: 269
<212> TYPE: PRT
<213> ORGANISM: Bacillus lentus

<400> SEQUENCE: 10

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

-continued

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

<210> SEQ ID NO 11
<211> LENGTH: 30
<212> TYPE: DNA
<213> ORGANISM: Artificial
<220> FEATURE:
<223> OTHER INFORMATION: upstream primer

<400> SEQUENCE: 11
atatgaattc gctgaggaag caaaagaaaa                                       30

<210> SEQ ID NO 12
<211> LENGTH: 31
<212> TYPE: DNA
<213> ORGANISM: Artificial
<220> FEATURE:
<223> OTHER INFORMATION: downstream primer

<400> SEQUENCE: 12
atatggatcc ttagcgtgtt gccgcttctg c                                     31

<210> SEQ ID NO 13
<211> LENGTH: 30
<212> TYPE: DNA
<213> ORGANISM: Artificial
<220> FEATURE:
<223> OTHER INFORMATION: upstream primer

<400> SEQUENCE: 13
atatgaattc gctgaggaag caaaagaaaa                                       30

<210> SEQ ID NO 14
<211> LENGTH: 31
<212> TYPE: DNA
<213> ORGANISM: Artificial
<220> FEATURE:
<223> OTHER INFORMATION: downstream primer

<400> SEQUENCE: 14
atatggatcc ttagcgcgtt gctgcatctg c                                     31

<210> SEQ ID NO 15
<211> LENGTH: 43

<212> TYPE: DNA
<213> ORGANISM: Artificial
<220> FEATURE:
<223> OTHER INFORMATION: upstream primer

<400> SEQUENCE: 15
atataagctt aaggaggata ttatgatgag gaaaaagagt ttt                43

<210> SEQ ID NO 16
<211> LENGTH: 34
<212> TYPE: DNA
<213> ORGANISM: Artificial
<220> FEATURE:
<223> OTHER INFORMATION: downstream primer

<400> SEQUENCE: 16
atatgaattc agctgcagaa gcggaatcgc tgaa                          34

<210> SEQ ID NO 17
<211> LENGTH: 43
<212> TYPE: DNA
<213> ORGANISM: Artificial
<220> FEATURE:
<223> OTHER INFORMATION: upstream primer

<400> SEQUENCE: 17
atataagctt aaggaggata ttatgaaaaa actattcaaa acc                43

<210> SEQ ID NO 18
<211> LENGTH: 34
<212> TYPE: DNA
<213> ORGANISM: Artificial
<220> FEATURE:
<223> OTHER INFORMATION: downstream primer

<400> SEQUENCE: 18
atatgaattc agcagccgcc gcagattgtg agaa                          34

<210> SEQ ID NO 19
<211> LENGTH: 43
<212> TYPE: DNA
<213> ORGANISM: Artificial
<220> FEATURE:
<223> OTHER INFORMATION: upstream primer

<400> SEQUENCE: 19
atataagctt aaggaggata ttatggcgaa accactatca aaa                43

<210> SEQ ID NO 20
<211> LENGTH: 34
<212> TYPE: DNA
<213> ORGANISM: Artificial
<220> FEATURE:
<223> OTHER INFORMATION: downstream primer

<400> SEQUENCE: 20
atatgaattc agcagcgtct gccgcgggta aacc                          34

<210> SEQ ID NO 21
<211> LENGTH: 43
<212> TYPE: DNA
<213> ORGANISM: Artificial
<220> FEATURE:
<223> OTHER INFORMATION: upstream primer

<400> SEQUENCE: 21

```
atataagctt aaggaggata ttatgacatt gactaaactg aaa                    43
```

<210> SEQ ID NO 22
<211> LENGTH: 34
<212> TYPE: DNA
<213> ORGANISM: Artificial
<220> FEATURE:
<223> OTHER INFORMATION: downstream primer

<400> SEQUENCE: 22

```
atatgaattc agcggcaagt gcctgactgg aaaa                              34
```

The invention claimed is:

1. An expression vector comprising:
   a) a promoter sequence; and
   b) a nucleic acid that encodes a protein comprising a signal peptide and a subtilisin, wherein the signal peptide comprises an amino acid sequence which is at least 95% identical to the amino acid sequence set forth in SEQ ID NO: 4, wherein the signal peptide is heterologous to the subtilisin, and
   wherein the expression vector achieves improved secretion of the protein from a host cell containing the expression vector as compared to secretion achieved by the expression vector having a signal peptide other than the signal peptide of b).

2. The expression vector of claim 1, wherein the signal peptide has the amino acid sequence of SEQ ID NO: 4.

3. The expression vector of claim 1, wherein the signal peptide is arranged N-terminal to the subtilisin in the protein encoded by the nucleic acid sequence b).

4. The expression vector of claim 1, wherein the protein encoded by the nucleic acid sequence b) further comprises a connecting sequence arranged between the signal peptide and the subtilisin sequence of the protein, the length of the connecting sequence consisting of between 1 and 50 amino acids.

5. The expression vector of claim 1, wherein the subtilisin comprises an amino acid sequence that is at least 95% identical to SEQ ID NO: 10 and has the amino acid glutamic acid (E) or aspartic acid (D) at position 99 in the numbering according to SEQ ID NO: 10.

6. A nonhuman host cell comprising the expression vector of claim 1.

7. The host cell of claim 6, wherein it is a bacterium.

8. A method for preparing a protein, comprising the steps of:
   (a) culturing the host cell of claim 6; and
   (b) isolating the protein from the culture medium or from the host cell.

9. The host cell of claim 7, wherein the bacterium is selected from the group consisting of the genera of *Escherichia*, *Klebsiella*, *Bacillus*, *Staphylococcus*, *Corynebacterium*, *Arthrobacter*, *Streptomyces*, *Stenotrophomonas* and *Pseudomonas*.

10. The host cell of claim 7, wherein the bacterium is selected from the group consisting of *Escherichia coli*, *Klebsiella planticola*, *Bacillus licheniformis*, *Bacillus lentus*, *Bacillus amyloliquefaciens*, *Bacillus subtilis*, *Bacillus alcalophilus*, *Bacillus globigii*, *Bacillus gibsonii*, *Bacillus clausii*, *Bacillus halodurans*, *Bacillus pumilus*, *Staphylococcus carnosus*, *Corynebacterium glutamicum*, *Arthrobacter oxidans*, *Streptomyces lividans*, *Streptomyces coelicolor*, and *Stenotrophomonas maltophilia*.

11. The expression vector of claim 1, wherein the expression vector achieves improved secretion of the protein from a host cell containing the expression vector as compared to secretion achieved by the expression vector having signal peptide SubC (*Bacillus licheniformis*).

* * * * *